United States Patent [19]

Wegner et al.

[11] Patent Number: 4,889,870

[45] Date of Patent: Dec. 26, 1989

[54] 2-(2,2-DIFLUOROCYCLOPROPYL)ALKYL ESTERS, PROCESSES FOR THEIR PREPARATION AND THEIR USE AS INSECTICIDES AND ACARICIDES

[75] Inventors: Peter Wegner; Hans-Rudolf Krüger; Dietrich Baumert; Hartmut Joppien, all of Berlin, Fed. Rep. of Germany

[73] Assignee: Schering Aktiengesellschaft, Fed. Rep. of Germany

[21] Appl. No.: 149,732

[22] Filed: Jan. 29, 1988

[30] Foreign Application Priority Data

Jan. 30, 1987 [DE] Fed. Rep. of Germany ....... 3703212

[51] Int. Cl.⁴ .................. A61K 31/325; A61K 31/34; C07C 69/24; C07D 307/45
[52] U.S. Cl. .................... 514/429; 514/452; 514/463; 514/522; 514/532; 514/533; 514/535; 514/538; 514/539; 514/544; 548/517; 549/362; 549/434; 558/414; 558/416; 560/10; 560/14; 560/17; 560/19
[58] Field of Search ............... 514/532, 544, 429, 452, 514/463, 522, 533, 535, 538, 539; 560/100, 106, 10, 14, 17, 19-23, 36, 45, 47, 48, 56, 59, 65, 73, 81, 83, 84, 101, 102, 104; 548/517; 549/362, 434; 558/414, 416

[56] References Cited

U.S. PATENT DOCUMENTS

| | | | |
|---|---|---|---|
| 3,993,774 | 11/1976 | Searle et al. | 514/531 |
| 4,198,527 | 4/1980 | Henrick | 560/124 |
| 4,376,784 | 3/1983 | Harney et al. | 514/532 |
| 4,459,305 | 7/1984 | Katsuda et al. | 560/124 |
| 4,611,010 | 9/1986 | Schwarz et al. | 514/521 |
| 4,757,086 | 7/1988 | Sirrenberg et al. | 514/452 |

*Primary Examiner*—Mary C. Lee
*Assistant Examiner*—Mary Sue Howard
*Attorney, Agent, or Firm*—Ostrolenk, Faber, Gerb & Soffen

[57] ABSTRACT

There are provided new 2-(2,2-difluorocyclopropyl)alkyl esters of general formula I

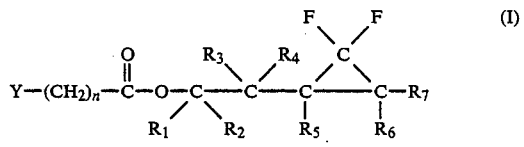

in which Y, $R_{1-7}$ and n have the meanings given in the description and processes for their preparation. The new compounds can be used to combat insects and mites.

18 Claims, No Drawings

2-(2,2-DIFLUOROCYCLOPROPYL)ALKYL ESTERS, PROCESSES FOR THEIR PREPARATION AND THEIR USE AS INSECTICIDES AND ACARICIDES

The invention relates to new 2-(2,2-difluorocyclopropyl)alkyl esters, their preparation and their use as pesticides with insecticidal and acaricidal activity.

It is already known that cyclopropane compounds possess acaricidal properties (USP 3 995 054).

The object of the present invention is to provide new compounds that combat insects and spider mites better than compounds known for this purpose.

It has now been found that 2-(2,2-difluorocyclopropyl)alkyl esters of general formula I

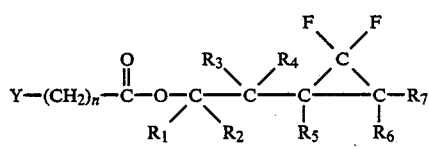

in which
Y is an aryl group, optionally substituted, one or more times, by $C_{1-6}$-alkyl, halo-$C_{1-6}$-alkyl, phenyl-$C_{1-6}$-alkyl, $C_{2-6}$-alkenyl, halo-$C_{2-6}$-alkenyl, phenyl-$C_{2-6}$-alkenyl, $C_{2-6}$-alkynyl, halo-$C_{2-6}$-alkynyl, phenyl-$C_{2-6}$-alkynyl, $C_{1-16}$-alkoxy, halo-$C_{1-6}$-alkoxy, phenyl-$C_{1-6}$-alkoxy, $C_{3-10}$-cycloalkoxy, halo-$C_{3-10}$-cycloalkoxy, phenyl-$C_{3-10}$-cycloalkoxy, $C_{3-6}$-cycloalkylalkoxy, halo-$C_{3-6}$-cycloalkylalkoxy, phenyl-$C_{3-6}$-cycloalkylalkoxy, $C_{2-6}$-alkenyloxy, halo-$C_{2-6}$-alkenyloxy, phenyl-$C_{2-6}$-alkenyloxy, $C_{2-6}$-alkynyloxy, halo-$C_{2-6}$-alkynyloxy, phenyl-$C_{2-6}$-alkynyloxy, alkylsulphonyloxy, haloalkylsulphonyloxy, arylsulphonyloxy, phenyl, halogen, amino, cyano, hydroxy, nitro, aryloxy, haloaryloxy, $C_{1-6}$-alkylaryloxy, nitroaryloxy, arylamino, haloarylamino, $C_{1-6}$-alkylarylamino, aryl-N-$C_{1-6}$-alkylamino, $C_{1-6}$-alkoxycarbonyl, halo-$C_{1-6}$-alkoxycarbonyl, phenyl-$C_{1-6}$-alkoxycarbonyl, $C_{3-10}$-cycloalkoxycarbonyl, halo-$C_{3-6}$-cycloalkoxycarbonyl, $C_{3-6}$-cycloalkylalkoxycarbonyl, halo-$C_{3-6}$-cycloalkylalkoxycarbonyl, phenyl-$C_{3-6}$-cycloalkylalkoxycarbonyl, $C_{1-2}$-alkyldioxy, alkyl-$C_{3-10}$-cycloalkoxy, $C_{1-6}$-alkylthio, halo-$C_{3-6}$-cycloalkylakylamino, $C_{1-6}$-alkylamino, di-$C_{1-6}$-alkylamino, N-pyrrolyl, the group $COOR_8$ ($R_8$ is hydrogen or a metal atom) or $N(R_9)_3X$ ($R_9$ is hydrogen or $C_{1-6}$-alkyl and X is halo),
$R_1$, $R_2$, $R_3$, $R_4$, $R_5$, $R_6$ and $R_7$ are the same or different and are hydrogen, $C_{1-6}$-alkyl, halo-$C_{1-6}$-alkyl, phenyl or halophenyl or $R_1$ and
$R_3$ can also together form an alicyclic ring, and
n is 0 or 1,
show a better insecticidal and acaricidal activity in comparison with known compounds.

The term aryl designated for Y in general formula I also embraces the groups 1-naphthyl, 2-naphthyl, 2-pyridyl, 3-pyridyl, 4-pyridyl, furan-2-yl, furan-3-yl, thiophen-2-yl, pyrrol-2-yl, pyrazin-2-yl, indol-2-yl, benzofuran-5-yl, benzothiophen-2-yl and 1,4-benzodioxan-2-yl.

2-(2,2-Difluorocyclopropyl)alkyl esters of general formula I which show particularly good activity are those where:
Y is phenyl, furanyl, thiophenyl, benzothiophenyl or naphthyl, or phenyl, furanyl, thiophenyl, benzothiophenyl, or naphthyl substituted one or more times by nitro, fluoro, chloro, bromo, $C_{1-6}$-alkyl, $C_{1-6}$-alkoxy, halo-$C_{3-6}$-cycloalkylalkoxy, phenyl, $C_{2-6}$-alkynyloxy or halo-$C_{2-6}$-alkenyloxy,
$R_{1-4}$ are hydrogen;
$R_{5-7}$ are hydrogen or methyl, and
n is 0 or 1.

The 2-(2,2-difluorocyclopropyl)alkyl esters of the invention of formula I can be prepared either
(A) by reacting an acid halide of general formula II

in which
Y has the meaning given in formula I
and X is chlorine or bromine,
with an alcohol of formula III

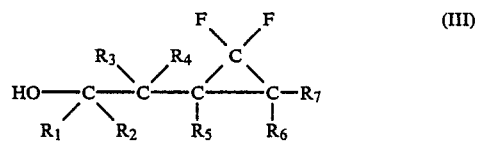

in which $R_{1-7}$ have the meanings given in formula I optionally using a solvent and in the presence of an acid acceptor, or
(B) by reacting a free acid of general formula IV

in which
Y has the meaning given in formula I, with an alcohol of formula III, optionally using a solvent as well as a catalyst, or
(C) by reacting a free acid of general formula IV, with an alcohol of formula V

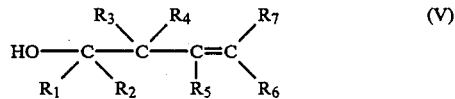

in which $R_{1-7}$ have the meanings given in formula I, optionally, using a solvent as well as a catalyst, to give an intermediate of formula VI

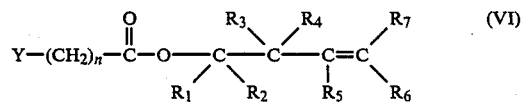

in which Y, n and $R_{1-7}$ have the meanings given in formula I, and reacting this with with difluorocarbene of formula [:$CF_2$], in the presence of an inert solvent.

Conventional basic materials are suitable as acid acceptors for reaction variant A), especially aliphatic, aromatic and heterocyclic amines, such as e.g. triethylamine, dimethylamine, piperidine, dimethylaniline, dimethylbenzylamine, pyridine and dimethylaminopyridine or inorganic bases such as oxides, hydroxides, carbonates, hydrogen carbonates and alcoholates of alkali- and alkaline earth metals, such as potassium hydroxide, sodium hydroxid, sodium and potassium carbonate.

Suitable solvents are the named acid acceptors themselves or inert solvents or mixtures of these.

Examples include aliphatic, alicyclic and aromatic hydrocarbons which can optionally be chorinated, such as hexane, cyclohexane, petroleum ether, benzene, toluene, xylene, dichloromethane, chloroform, carbon tetrachloride, 1,2-dichloroethane, trichloroethylene and chlorobenzene; ethers, such as diethyl ether, methyl ethyl ether, diisopropyl ether, dibutyl ether, dioxane and tetrahydrofuran; ketones, such as acetone, methyl ethyl ketone, methyl isopropyl ketone and methyl isobutyl ketone; nitriles, such as acetonitrile, propionitrile and benzonitrile, esters, such as ethyl acetate and amyl acetate, amides, such as dimethylformamide and dimethylacetamide, as well as sulphones and sulphoxides, such as dimethyl sulphoxide and sulpholane.

The reaction can be carried out within a wide temperature range. In general it is carried out at a temperature between −20° C. and the boiling point of the reaction mixture, preferably between 20° and 200° C.

The reaction can be carried out at normal pressure, or even at higher or reduced pressure.

Catalysts which are suitable for carrying out reaction variant B include strong acids, such as sulphuric acid, hydrogen halides, sulphonic acids and acidic ion exchange reagents. It is advantageous if water or the ester of formula I is removed from the reaction mixture, for example by azeotropic distillation or by binding the water to sulphuric acid or a hydrogen halide acid.

Reaction variant B can be carried out under similar reaction conditions as far as temperature and pressure are concerned, and in the same solvents or mixtures thereof, as for reaction variant A.

For the preparation of the intermediate compound VI, used in reaction variant C, the same acid catalysts and inert solvents named for reaction variant B can be used. The carbene reaction is however preferably carried out in an ether, such as diglyme, triglyme or tetraglyme. The production of difluorocarbene can be carried according to well known methods in the technical literature (Burton and Hahnfeld, Fluorine Chem. Rev. 8 (1977), 119 ff).

Suitable substances for generating difluorcarbene are for example alkali metal chlorodifluoroacetates, such as sodium chlorodifluoroacetate; halodifluorohydrocarbons, such as chlorodifluoromethane; organo tin compounds, such as trimethyl(trifluoromethyl)tin; organo mercury compounds, such as phenyl(trifluoromethyl)mercury; and organo phosphorus compounds such tris(trifluoromethyl)difluorophosphorane and triphenyl(bromodifluoromethyl)phosphonium bromide.

The compounds of the invention prepared by the above described processes can be isolated from the reaction mixture in conventional manner, for example by distillation of the solvent used at normal or reduced pressure, by precipitation with water or by extraction.

A higher degree of purity can be achieved as general rule by thin layer chromatography purification, by fractional distillation or recrystallisation.

The compounds of the invention are, as a rule, almost colourless and odourless viscous oils or crystals that are almost insoluble in water, have limited solubility in aliphatic hydrocarbons, such as petroleum ether, hexane, pentane and cyclohexane, and highly soluble in chlorinated hydrocarbons, such as chloroform, methylene dichloride and carbon tetrachloride, aromatic hydrocarbons such as benzene, toluene and xylene, ethers, such as diethyl ether, tetrahydrofuran and dioxane, nitriles, such as acetonitrile, alcohols, such as methanol and ethanol, amides, such as dimethylformamide, and sulphoxides, such as dimethyl sulphoxide.

The acid halides formula II and acids of formula IV, as well as the alcohols of formula III and V, used as starting materials, are known or can be prepared by known methods.

The compounds of the invention have insecticidal and acaricidal activity and as a result can be used for combating a wide range of insectes and acarids, including animal ectoparasites. Examples include Lepidoptera, such as *Plutella xylostella, Spodoptera littoralis, Heliothis armigera* and *Pieris brassicae*; Diptera, such as *Musca domestica, Ceratitis capitata, Erioischia brassicae, Lucilia sericata* and *Aedes aegypti*; Homoptera, including aphids such as *Meqoura viciae* and *Nilaparvata lugens*; Coleoptera, such as *Phaedon cochleariae, Anthonomus grandis, Epilachna varivestis* and corn rootworms (Diabrotica spp. eg. *Diabrotica undecimpunctata*); Orthoptera, such as *Blattella germanica*; ticks, such as *Boophilus microplus* and lice, such as *Damalinia bovis* and *Linognathus vituli*, as well as spider mites such as *Tetranychus urticae* and *Panonychus ulmi*.

The compounds of the invention are distinguished by good insecticidal activity and especially good acaricidal activity and thus represent a valuable improvement in the state of the art.

The compounds according to the invention can be used at a concentration of 0.0005 to 5%, preferably from 0.001 to 1%, calculated as gram active material per 100 ml of the composition.

The compounds of the invention can be used either alone or in mixture with each other or another insecticide. Optionally other plant protection or pesticidal compositions, such as for example insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose.

Suitable mixture partners may also include phospholipids, e.g. such as from the group phosphatidylcholine, hydrated phosphatidylcholine, phosphatidylethanolamine, N-acyl-phosphatidylethanolamine, phosphatidylinositol, phosphatidylserine, lysolecithin or phosphatidylglycerol.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons such as benzene, toluene, xylene, cyclohexanone, isophorone, dimethyl sulphoxide, dimethylformamide, other mineral-oil fractions and plant oils.

Suitable solid carriers include mineral earths, e.g. tonsil, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

Formulations can be prepared, for example, from the following ingredients.

A. WETTABLE POWDER
20 percent by weight active ingredient
35 percent by weight bentonite
8 percent by weight calcium lignosulphonate
2 percent by weight of the sodium salt of N-methyl-N-oleyltaurine
35 percent by weight silicic acid B. PASTE
45 percent by weight active ingredient
5 percent by weight sodium aluminium silicate
15 percent by weight cetylpolyglycol ether with 8 moles ethylene oxide
2 percent by weight spindle oil
10 percent by weight polyethylene glycol
23 parts water C. EMULSIFIABLE CONCENTRATE
20 percent by weight active ingredient
75 percent by weight isophorone
5 percent by weight of a mixture based on the sodium salt of N-methyl-N-oleyltaurine and calcium lignosulphonate

EXAMPLE 1

2-(2,2-Difluorocyclopropyl)ethyl benzoate 11 g (62 mmol) 3-Butenyl benzoate was dissolved in 50 ml diethylene glycol dimethyl ether (diglyme) and reacted at 165° C. over 4 hours with a solution of 19 g (62 mmol) sodium chlorodifluoroacetate, dissolved in 50 ml diglyme. The mixture was then stirred for an hour at 165° C. and cooled. The precipitated sodium chloride was removed and washed in 100 ml diglyme. The filtrate was concentrated in vacuo (35° C., oil pump) and the residue taken up in 100 ml ether, the extract washed twice each time with 20 ml water and dried over magnesium sulphate. After evaporation it was fractionated under an oil pump vacuum, on a spiny column.

Yield: 12.8 g (91% of theory).
TLC: Eluent=hexane:ethyl acetate=8:2, $R_f$=0.51.
b.p./0.1: 83°–84° C.
$n_D^{20}$: 1.4845.

PREPARATION OF THE STARTING MATERIAL

3-Butenyl benzoate 5 g (70 mmol) 3-Buten-1-ol, 9.7 ml (70 mmol) triethylamine and 95 mg dimethylaminopyridine, dissolved in 25 ml tetrahydrofuran, was reacted, with ice cooling at 35° C., with 7.5 ml (65 mmol) benzoyl chloride. The mixture was stirred for 2 hours at room temperature, poured into 80 ml water and extracted 3 times each time with 50 ml ether. The combined ether phase was washed twice each time with 20 ml water and dried over magnesium sulphate. After evaporation of the solvent it was dried using an oil pump vacuum at 30° C. The resulting oil was used without further purification.

Yield: 11 g (96% of theory).
TLC: Eluent=hexane:ethyl acetate=8:2, $R_f$=0.54.
$n_D^{20}$: 1.5099.

EXAMPLE 2

2-(2,2-Difluorocyclopropyl)ethyl 3,5-dinitrobenzoate 3,5-Dinitrobenzoyl chloride, dissolved in 10 ml THF, was added dropwise to a solution of 2 g (16 mmol) 2-(2,2-difluorocyclopropyl)ethanol, 2.3 ml (16 mmol) triethylamine and 400 mg dimethylaminopyridine in 30 ml tetrahydrofuran (THF) at 0° C. and the mixture stirred for 2 hours at room temperature. The precipitate was removed and the solution concentrated in vacuo, (about 200 mbar). The residue was purified by column chromotography (silica gel, hexane/ethyl acetate=95:5).

Yield: 2 g (39% of theory).
TLC: Eluent=hexane:ethyl acetate =8:2, $R_f$=0.46.
m.p.: 87° C.

PREPARATION OF THE STARTING MATERIAL 2-(2,2-Difluorocyclopropyl)ethanol 38.5 g (170 mmol) 2-(2,2-Difluorocyclopropyl)ethyl benzoate was added dropwise to a solution of 17.2 g (430 mmol) sodium hydroxide in 170 ml methanol/water (3:2) and the mixture stirred at room temperature (RT) for 2 hours. It was then poured into 170 ml saturated NaCl solution and extracted 4 times each time with 100 ml ether. The combined ether phase was dried over magnesium sulphate and concentrated at 40° C. at atmospheric pressure. It was then fractionated under vacuum (about 200 mbar).

Yield: 16.6 g (79% of theory).
TLC: Eluent =hexane:ethyl acetate=8:2, $R_f$=0.21.
b.p./200 mbar: 115° C.
$n_D^{20}$: 1.3904.

EXAMPLE 3

2-(2,2-Difluorocyclopropyl)ethyl 2,6-dimethoxybenzoate

A solution of 3.5 g (13.6 mmol) triphenylphosphine and 2.5 g (20 mmol) 2-(2,2-difluorocyclopropyl)ethanol in 30 ml ether was added dropwise at RT to a solution of 2.48 g (13.6 mmol) 2,6-dimethoxybenzoic acid and 2.35 g (13.6 mmol) diethyl azodicarboxylate in 30 ml ether. The mixture was stirred for 6 hours at RT and allowed to stand overnight. After evaporation of the solvent, the residue was chromatographed over silica gel (hexane/ethyl acetate =95:5).

Yield: 3 g (77% of theory).
TLC: Eluent=hexane:ethyl acetate=8:2, $R_f$=0.26.
$n_D^{20}$: 1.4974.

In a similar manner to Examples 1 to 3 the following compounds of the invention were prepared.

| Example | Compound | Physical Constant $n_D^{20}$/m.p.(°C.) |
|---|---|---|
| 4 | 2-(2,2-Difluorocyclopropyl)ethyl 2,4-dichlorobenzoate | 1.5173 |
| 5 | 2-(2,2-Difluorocyclopropyl)ethyl 3,4-dichlorobenzoate | 1.5178 |
| 6 | 2-(2,2-Difluorocyclopropyl)ethyl 2-chlorobenzoate | 1.5010 |
| 7 | 2-(2,2-Difluorocyclopropyl)ethyl 4-nitrobenzoate | 67–68 |
| 8 | 2-(2,2-Difluorocyclopropyl)ethyl 2-methylbenzoate | 1.4908 |
| 9 | 2-(2,2-Difluorocyclopropyl)ethyl 3,4-dimethylbenzoate | 1.4965 |
| 10 | 2-(2,2-Difluorocyclopropyl)ethyl | 1.4738 |

| Example | Compound | Physical Constant $n_D^{20}$/m.p.(°C.) |
|---|---|---|
| 11 | 2-(2,2-Difluorocyclopropyl)ethyl 4-ethoxybenzoate | 1.5007 |
| 12 | Di-[2-(2,2-difluorocyclopropyl)-ethyl] terephthalate | 55–56 |
| 13 | 2-(2,2-Difluorocyclopropyl)ethyl 2,6-dichlorobenzoate | 1.5055 |
| 14 | 2-(2,2-Difluorocyclopropyl)ethyl 4-chlorobenzoate | 1.5065 |
| 15 | 2-(2,2-Difluorocyclopropyl)ethyl 4-bromobenzoate | 1.5203 |
| 16 | 2-(2,2-Difluorocyclopropyl)ethyl phenylacetate | 1.4806 |
| 17 | 2-(2,2-Difluorocyclopropyl)ethyl furan-2-carboxylate | 1.4647 |
| 18 | 2-(2,2-Difluorocyclopropyl)ethyl pentafluorobenzoate | 1.4343 |
| 19 | 2-(2,2-Difluorocyclopropyl)ethyl 2,4-dimethylbenzoate | 1.4934 |
| 20 | 2-(2,2-Difluorocyclopropyl)ethyl 4-chloro-2-nitrobenzoate | 1.5158 |
| 21 | 2-(2,2-Difluorocyclopropyl)ethyl 4-methoxybenzoate | 1.5002 |
| 22 | 2-(2,2-Difluorocyclopropyl)ethyl 2-ethoxybenzoate | 1.4906 |
| 23 | 2-(2,2-Difluorocyclopropyl)ethyl 2-nitrobenzoate | 1.5017 |
| 24 | 2-(2,2-Difluorocyclopropyl)ethyl 3-nitrobenzoate | 1.5099 |
| 25 | 2-(2,2-Difluorocyclopropyl)ethyl 2-methyl-3-nitrobenzoate | 1.5077 |
| 26 | 2-(2,2-Difluorocyclopropyl)ethyl 3-methyl-4-nitrobenzoate | 1.5120 |
| 27 | 2-(2,2-Difluorocyclopropyl)ethyl 3,4-dinitrobenzoate | 63 |
| 28 | 2-(2,2-Difluorocyclopropyl)ethyl 2-methoxybenzoate | 1.4984 |
| 29 | 2-(2,2-Difluoro-1-methylcyclopropyl)-ethyl benzoate | 1.4856 |
| 30 | 2-(2,2-Difluorocyclopropyl)ethyl 4-methylbenzoate | 1.4892 |
| 31 | 2-(2,2-Difluorocyclopropyl)ethyl 4-cyanobenzoate | 1.5052 |
| 32 | 2-(2,2-Difluorocyclopropyl)ethyl 3-trifluoromethylbenzoate | 1.4472 |
| 33 | 2-(2,2-Difluorocyclopropyl)ethyl 4-nitrophenylacetate | 1.5092 |
| 34 | 2-(2,2-Difluorocyclopropyl)ethyl 4-hydroxyphenylacetate | 1.5071 |
| 35 | 2-(2,2-Difluorocyclopropyl)ethyl 4-[2-(2,2-difluorocyclopropyl)-ethoxy]benzoate | 54–55 |
| 36 | 2-(2,2-Difluoro-1-methylcyclopropyl)-ethyl 4-nitrobenzoate | 75–76 |
| 37 | 2-(2,2-Difluoro-1-methylcyclopropyl)-ethyl 4-ethoxybenzoate | 1.4986 |
| 38 | 2-(2,2-Difluorocyclopropyl)ethyl 4,5-diphenylthiophene-2-carboxylate | 1.6050 |
| 39 | 2-(2,2-Difluorocyclopropyl)ethyl 2-chlorophenylacetate | 1.4938 |
| 40 | 2-(2,2-Difluorocyclopropyl)ethyl 4-chlorophenylacetate | 1.4935 |
| 41 | 2-(2,2-Difluorocyclopropyl)ethyl 4-methoxyphenylacetate | 1.4889 |
| 42 | 2-(2,2-Difluorocyclopropyl)ethyl furan-3-carboxylate | 1.4522 |
| 43 | 2-(2,2-Difluorocyclopropyl)ethyl 5-nitrofuran-2-carboxylate | 78–79 |
| 44 | 2-(2,2-Difluorocyclopropyl)ethyl N—methylpyrrole-2-carboxylate | 1.4854 |
| 45 | 2-(2,2-Difluorocyclopropyl)ethyl pyrazine-2-carboxylate | 1.4855 |
| 46 | 2-(2,2-Difluorocyclopropyl)ethyl 2-chloronicotinate | 1.5008 |
| 47 | 2-(2,2-Difluorocyclopropyl)ethyl 3-chlorobenzo[b]thiophene-2-carboxylate | 1.5736 |
| 48 | 2-(2,2-Difluorocyclopropyl)ethyl 7-nitroindole-2-carboxylate | 71–72 |
| 49 | 2-(2,2-Difluorocyclopropyl)ethyl thiophene-2-carboxylate | 1.4979 |
| 50 | 2-(2,2-Difluorocyclopropyl)ethyl 2-naphthylacetate | 1.5554 |
| 51 | 2-(2,2-Difluorocyclopropyl)ethyl 1-naphthalatate | 1.5552 |
| 52 | 2-(2,2-Difluorocyclopropyl)ethyl 2-naphthalatate | 1.5576 |
| 53 | 2-(2,2-Difluorocyclopropyl)ethyl 2-trifluoromethylbenzoate | 1.4491 |
| 54 | 2-(2,2-Difluorocyclopropyl)ethyl pyrrole-2-carboxylate | 64/65–66 |
| 55 | Trans-2-(3-ethyl-2,2-difluoro-cyclopropyl)ethyl benzoate | 1.4799 |
| 56 | Cis-2-(3-ethyl-2,2-difluoro-cyclopropyl)ethyl benzoate | 1.4835 |
| 57 | 2-(2,2-Difluoro-1-methylcyclopropyl)-5-methylcyclohexyl benzoate | 1.4958 |
| 58 | 2-(2,2-Difluorocyclopropyl)ethyl picolinate | 1.4871 |
| 59 | 2-(2,2-Difluorocyclopropyl)ethyl nicotinate | 1.4847 |
| 60 | 2-(2,2-Difluorocyclopropyl)ethyl isonicotinate | 1.4828 |
| 61 | 2-(2,2-Difluorocyclopropyl)ethyl 4-trifluoromethylbenzoate | 1.4475 |
| 62 | 2-(2,2-Difluorocyclopropyl)ethyl 2,4,6-trimethylbenzoate | 1.4870 |
| 63 | Trans-2-(3-ethyl-2,2-difluoro-cyclopropyl)ethyl 4-nitrobenzoate | 1.5033 |
| 64 | Trans-2-(3-ethyl-2,2-difluoro-cyclopropyl)ethyl 4-ethoxybenzoate | 1.4924 |
| 65 | Cis-2-(3-ethyl-2,2-difluoro-cyclopropyl)ethyl 4-nitrobenzoate | 1.5068 |
| 66 | Cis-2-(3-ethyl-2,2-difluoro-cyclopropyl)ethyl 4-ethoxybenzoate | 1.4959 |
| 67 | 2-(2,2-Difluorocyclopropyl)ethyl 2-phenylbenzoate | 1.5420 |
| 68 | 2-(2,2-Difluoro-1-methylcyclopropyl)-5-methylcyclohexyl 4-nitrobenzoate | 106–107 |
| 69 | 2-(2,2-Difluoro-1-methylcyclopropyl)-5-methylcyclohexyl 4-ethoxybenzoate | 1.4972 |
| 70 | 2-(2,2-Difluorocyclopropyl)ethyl 4-butoxybenzoate | 1.4952 |
| 71 | 2-(2,2-Difluorocyclopropyl)ethyl 3,4-methylenedioxybenzoate | 1.5139 |
| 72 | 2-(2,2-Difluorocyclopropyl)ethyl 4-(2-isopropyl-5-methylcyclohexyl-oxy)benzoate | 1.4921 |
| 73 | 2-(2,2-Difluorocyclopropyl)ethyl 4-[1-(4-chlorophenyl)-1-cyclopropyl)-methoxy]benzoate | 1.5467 |
| 74 | 2-(2,2-Difluorocyclopropyl)ethyl 3,4-dihydroxybenzoate | 84–85 |
| 75 | 2-(2,2-Difluorocyclopropyl)ethyl 3,4-ethylenedioxybenzoate | 1.5184 |
| 76 | 2-(2,2-Difluorocyclopropyl)ethyl 4-(2,2,2-trifluorethoxy)benzoate | 1.4632 |
| 77 | 2-(2,2-Difluorocyclopropyl)ethyl 4-(2-propen-1-yloxy)benzoate | 1.5078 |
| 78 | 2-(2,2-Difluorocyclopropyl)ethyl 4-(2-propyn-1-yloxy)benzoate | 1.5125 |
| 79 | 2-(2,2-Difluorocyclopropyl)ethyl 4-isopropoxybenzoate | 1.4944 |
| 80 | 2-(2,2-Difluorocyclopropyl)ethyl 4-trifluoromethyl-sulphonyloxybenzoate | 1.4551 |
| 81 | 2-(2,2-Difluorocyclopropyl)ethyl 4-(2,2-dichlorovinyloxy)benzoate | 1.5207 |
| 82 | 2-(2,2-Difluorocyclopropyl)ethyl 3-fluoro-4-hydroxyphenylacetate | 1.4868 |
| 83 | 2-(2,2-Difluorocyclopropyl)ethyl 3-fluoro-4-methoxyphenylacetate | 1.4813 |
| 84 | 2-(2,2-Difluorocyclopropyl)ethyl 4-ethoxy-3-fluorophenylacetate | 1.4803 |
| 85 | 2-(2,2-Difluorocyclopropyl)ethyl 4-methylthiobenzoate | 1.5450 |
| 86 | 2-(2,2-Difluorocyclopropyl)ethyl 4-ethylthiobenzoate | 1.5381 |
| 87 | 2-(2,2-Difluorocyclopropyl)ethyl 4-(1,1,2,2-tetrafluoroethoxy)benzoate | 1.4447 |

-continued

| Example | Compound | Physical Constant $n_D^{20}$/m.p.(°C.) |
|---|---|---|
| 88 | 2-(2,2-Difluorocyclopropyl)ethyl 4-trifluormethoxybenzoate | 1.4442 |
| 89 | 2-(2,2-Difluorocyclopropyl)ethyl 4-aminobenzoate | 1.5476 |
| 90 | N,N—Dimethyl-N'-4-[2-(2,2-difluorocyclopropyl)ethoxycarbonyl]phenyl-formamidine | 1.5685 |
| 91 | 2-(2,2-Difluorocyclopropyl)ethyl 4-tert-butylbenzoate | 1.4893 |
| 92 | 2-(2,2-Difluorocyclopropyl)ethyl 4-dimethylaminobenzoate | 1.5481 |
| 93 | 2-(2,2-Difluorocyclopropyl)ethyl 2,4,6-triisopropylbenzoate | 1.4822 |
| 94 | 2-(2,2-Difluorocyclopropyl)ethyl 4-aminobenzoate, hydrochloride | 172–180 |
| 95 | 2-(2,2-Difluorocyclopropyl)ethyl 4-hexadecyloxybenzoate | 53–54 |
| 96 | 2-(2,2-Difluorocyclopropyl)ethyl 4-hexyloxybenzoate | 1.4943 |
| 97 | Sodium 2-(2,2-difluorocyclopropyl)-ethyl phthalate | 175–180 |
| 98 | N-4-[2-(2,2-difluorocyclopropyl)-ethoxycarbonyl]phenyl trimethyl-ammonium iodide | 149 |
| 99 | 2-(2,2-Difluorocyclopropyl)ethyl-phthalate | 1.5041 |
| 100 | 2-(2,2-Difluorocyclopropyl)ethyl 4-(1-pyrrolyl)benzoate | 61–62 |
| 101 | 2-(2,2-Difluorocyclopropyl)-1-methyl-ethyl 4-butoxybenzoate | 1.4919 |
| 102 | 2-(2,2-Difluorocyclopropyl)-1-methyl-ethyl 4-nitrobenzoate | 1.5073 |
| 103 | 2-(2,2-Difluorocyclopropyl)-1-methyl-ethyl benzoate | 1.4821 |

The following Examples illustrate the biological activity of the compounds of the invention

TEST EXAMPLE 1

Insecticidal activity against motile stages of the two spotted mite (*Tetranychus urticae*)

The compounds of the invention were made up as aqueous emulsions at a concentration of 0.1%. Potted field beans plants (*Phaseolus vulgaris*), in the primary leaf stage, artificially infested with spider mites (*Tetranychus urticae*) were sprayed with these preparations until dripping wet and left in a laboratory under extended daylight conditios for 7 days. After this, the mortality in % of the motile stages, in comparison with untreated controls, was determined with the aid of a magnifying glass.

The compounds of the invention of Examples 1–7, 9, 11, 12, 20–27, 34, 35, 38, 40, 41, 43, 44, 90–96 and 100 produced 100% mortality of motile stages of the two spotted mite (*Tetranychus urticae*).

TEST EXAMPLE 2

Insecticidal activity against eggs of the two spotted mite (*Tetranychus urticae*)

The compounds of the invention were made up as aqueous emulsions at a concentration of 0.1%. Potted field beans plants (*Phaseolus vulgaris*, variety "Saxa"), in the primary leaf stage, artificially infested with fertile female spider mites (*Tetranychus urticae*) were sprayed with these preparations until dripping wet and left in a laboratory under extended daylight conditios for 7 days. After this, the mortality in % of the motile stages, in comparison with untreated controls, was determined with the aid of a magnifying glass.

The compounds of the invention of Examples 4, 5, 7, 9, 11, 30, 31, 34, 35, 38–41, 43, 44, 90–92, 94–96 and 100 produced 100% mortality of eggs of the two spotted mite (*Tetranychus urticae*).

TEST EXAMPLE 3

Insecticidal activity against *Musca domestica*

Aliquots of acetone solutions of test compounds at various concentrations were applied to 9 cm diameter filter papers placed in the bottom of 9 cm diameter petri dishes closed by glass lids. After evaporation of solvent, the treated surfaces, together with control treated with acetone alone, were then infested with adult houseflies, (*Musca domestica*) and held at 22° C. for 24 hours. The percentage mortality of the insects was then recorded.

Less than 5% mortality resulted in the control treatments whereas the compounds of Examples 1, 4, 8, 14, 16, 18, 30, 32, 33, 36, 56, 61 and 62 had an $LC_{50}$ of 1000 mg/m$^2$ or less.

TEST EXAMPLE 4

Insecticidal activity against *Lucilia sericata*

1 ml aliquots of an acetone solution containing test compound at various concentrations were applied to cotton wool dental rolls 1 cm×2 cm, contained in glass vials (2 cm diameter ×5 cm long). After drying, the treated materials were then impregnated with 1 ml of nutrient solution, infested with first instar larvae of sheep blowfly (*Lucilia sericata*), closed by a cotton wool plug and held at 25° C. for 24 hours.

For the controls the mortality was <5% whereas the compounds of Examples 32, 33 and 95 had an $LC_{50}$ of 100 ppm or less.

TEST EXAMPLE 5

Insecticidal activity against *Blattella germanica*

Aliquots of acetone solutions of test compounds at various concentrations were applied to glass plates (10 cm ×10 cm). After evaporation of solvent, the treated surfaces, together with controls treated with acetone alone, were then infested with second instar nymphs of the German cockroach, (*Blattella germanica*), retained on the treated surface within PTFE-coated glass rings 6 cm in diameter and held for 24 hours at 22° C. The percentage mortality of the insects was then recorded.

Less than 5% mortality resulted in the control treatments whereas the compounds of Examples 40, 82 and 85 had an $LD_{50}$ of 100 mg/m$^2$ or less.

TEST EXAMPLE 6

Tickicidal activity against Boophilus microplus 9 cm diameter filter papers were impregnated with 1 ml aliquots of acetone solutions of test compound at various concentrations. The papers were allowed to dry and then folded into envelopes in which cattle tick larvae, (*Boophilus microplus*) were enclosed and held at 25° C. and 80% R.H. for 48 hours. The percentage mortality of tick larvae was then recorded and compared with controls.

The controls gave a mortality of less than 5% whereas compounds of Examples 1 and 51 caused 50% mortality at a concentration of 300 ppm or less.

We claim:

1. 2-(2,2-Difluorocyclopropyl)alkyl esters of general formula I

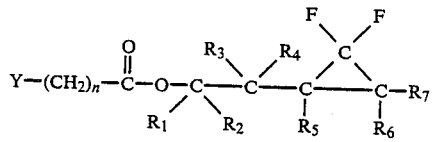

in which

Y is an aryl group, unsubstituted or substituted, one or more times, by $C_{1-6}$-alkyl, halo-$C_{1-6}$-alkyl, phenyl-$C_{1-6}$-alkyl, $C_{2-6}$-alkenyl, halo-$C_{2-6}$-alkenyl, phenyl-$C_{2-6}$-alkenyl, $C_{2-6}$-alkynyl, halo-$C_{2-6}$-alkynyl, phenyl-$C_{2-6}$-alkynyl, $C_{1-16}$-alkoxy, halo-$C_{1-6}$-alkoxy, phenyl-$C_{1-6}$-alkoxy, $C_{3-10}$-cycloalkoxy, halo-$C_{3-10}$-cycloalkoxy, phenyl-$C_{3-10}$-cycloalkoxy, $C_{3-6}$-cycloalkylalkoxy, halo-$C_{3-6}$-cycloalkylalkoxy, phenyl-$C_{3-6}$-cycloalkylalkoxy, $C_{2-6}$-alkenyloxy, halo-$C_{2-6}$-alkenyloxy, phenyl-$C_{2-6}$-alkenyloxy, $C_{2-6}$-alkynyloxy, halo-$C_{2-6}$-alkynyloxy, phenyl-$C_{2-6}$-alkynyloxy, alkylsulphonyloxy, haloalkylsulphonyloxy, arylsulphonyloxy, phenyl, halogen, amino, cyano, hydroxy, nitro, aryloxy, haloaryloxy, $C_{1-6}$-alkylaryloxy, nitroaryloxy, arylamino, haloarylamino, $C_{1-6}$-alkylarylamino, aryl-N-$C_{1-6}$-alkylamino, $C_{1-6}$-alkoxycarbonyl, halo-$C_{1-6}$-alkoxycarbonyl, phenyl-$C_{1-6}$-alkoxycarbonyl, $C_{3-10}$-cycloalkoxycarbonyl, halo-$C_{3-6}$-cycloalkoxycarbonyl, $C_{3-6}$-cycloalkylalkoxycarbonyl, halo-$C_{3-6}$-cycloalkylalkoxycarbonyl, phenyl-$C_{3-6}$-cycloalkylalkoxycarbonyl, $C_{1-2}$-alkyldioxy, alkyl-$C_{3-10}$-cycloalkoxy, $C_{1-6}$-alkylthio, halo-$C_{3-6}$-cycloalkylalkylamino, $C_{1-6}$-alkylamino, di-$C_{1-6}$-alkylamino, N-pyrrolyl, the group $COOR_8$ ($R_8$ is hydrogen or a metal atom) or $N(R_9)_3X$ ($R_9$ is hydrogen or $C_{1-6}$-alkyl and X is halo), $R_1$, $R_2$, $R_3$, $R_4$, $R_5$, $R_6$ and $R_7$ are the same or different and are hydrogen, $C_{1-6}$-alkyl, halo-$C_{1-6}$-alkyl, phenyl or halophenyl and n is 0 or 1.

2. 2-(2,2-Difluorocyclopropyl)alkyl esters according to claim 1, characterised in that Y is phenyl or naphthyl, unsubstituted or substituted one or more times by nitro, fluoro, chloro, bromo, $C_{1-6}$-alkyl, $C_{1-6}$-alkoxy, halo-$C_{3-6}$-cycloalkylalkoxy, phenyl, $C_{2-6}$-alkynyloxy or halo-$C_{2-6}$-alkenyloxy, $R_{1-4}$ are hydrogen; and $R_{5-7}$ are hydrogen or methyl, and n is 0 or 1.

3. An insecticidal and acaricidal composition which comprises a compound claimed in claim 1, in admixture with an agriculturally acceptable diluent or carrier.

4. A method of combating insects and acarids which comprises applying to the insects or acarids or their locus an effective amount of a compound claimed in claim 1.

5. An insecticidal and acaricidal composition which comprises a compound claimed in claim 2, in admixture with an agriculturally acceptable diluent or carrier.

6. A method of combating insects and acarids which comprises applying to the insects or acarids or their locus an effective amount of a compound claimed in claim 2.

7. 2-(2,2-Difluorocyclopropyl)alkyl esters according to claim 2, characterized in that Y is phenyl or phenyl substituted by chloro or alkyl.

8. 2-(2,2-Difluorocyclopropyl)alkyl esters according to claim 7 in which Y is phenyl substituted by one or two chloro atoms.

9. 2-(2,2-Difluorocyclopropyl)alkyl esters according to claim 7, characterized in that Y is phenyl substituted one or more times by $C_{1-6}$-alkyl.

10. 2-(2,2-Difluorocyclopropyl)alkyl esters according to claim 9, characterized in that Y is 4-isopropylphenyl and n is 0.

11. An insecticidal and acaricidal composition which comprises a compound claimed in claim 7, in admixture with an agricultrually acceptable diluent or carrier.

12. An insecticidal and acaricidal composition which comprises a compound claimed in claim 8, in admixture with an agricultrually acceptable diluent or carrier.

13. An insecticidal and acaricidal composition which comprises a compound claimed in claim 9, in admixture with an agricultrually acceptable diluent or carrier.

14. An insecticidal and acaricidal composition which comprises a compound claimed in claim 10, in admixture with an agricultrually acceptable diluent or carrier.

15. A method of combatting insects and acarids which comprises applying to the insects or acarids or their locus an effective amount of a compound claimed in claim 7.

16. A method of combatting insects and acarids which comprises applying to the insects or acarids or their locus an effective amount of a compound claimed in claim 8.

17. A method of combatting insects and acarids which comprises applying to the insects or acarids or their locus an effective amount of a compound claimed in claim 9.

18. A method of combatting insects and acarids which comprises applying to the insects or acarids or their locus an effective amount of a compound claimed in claim 10.

* * * * *